(12) United States Patent
Faccioli et al.

(10) Patent No.: US 9,131,924 B2
(45) Date of Patent: Sep. 15, 2015

(54) SURGICAL DEVICE

(75) Inventors: Giovanni Faccioli, Monzambano (IT); Renzo Soffiatti, Nogara (IT)

(73) Assignee: TECRES S.P.A., Sommacampagna (Verona) (IT)

( * ) Notice: Subject to any disclaimer, the term of this patent is extended or adjusted under 35 U.S.C. 154(b) by 389 days.

(21) Appl. No.: 12/994,609

(22) PCT Filed: Apr. 16, 2009

(86) PCT No.: PCT/IB2009/051587
§ 371 (c)(1),
(2), (4) Date: Nov. 24, 2010

(87) PCT Pub. No.: WO2009/150554
PCT Pub. Date: Dec. 17, 2009

(65) Prior Publication Data
US 2011/0071535 A1    Mar. 24, 2011

(30) Foreign Application Priority Data
Jun. 11, 2008    (IT) .............................. VR2008A0067

(51) Int. Cl.
*A61B 17/56* (2006.01)
*A61B 10/02* (2006.01)
*A61B 17/88* (2006.01)
*A61B 17/34* (2006.01)
*A61B 17/00* (2006.01)

(52) U.S. Cl.
CPC ........... *A61B 10/025* (2013.01); *A61B 17/8811* (2013.01); *A61B 17/8819* (2013.01); *A61B 17/3417* (2013.01); *A61B 2010/0258* (2013.01); *A61B 2017/00455* (2013.01); *A61B 2017/00477* (2013.01)

(58) Field of Classification Search
CPC ............. A61B 10/025; A61B 17/8811; A61B 17/8819; A61B 17/3417; A61B 2017/00477; A61B 2017/00455; A61B 2010/0258
USPC ...................................... 606/92, 93; 604/187
See application file for complete search history.

(56) References Cited

U.S. PATENT DOCUMENTS 2,701,378 A * 2/1955 Dugan et al. .................... 15/111
2,855,661 A * 10/1958 Forster ......................... 29/240.5
(Continued)

FOREIGN PATENT DOCUMENTS

EP          1350478 A1   10/2003
WO    WO 02065926 A1    8/2002
(Continued)

*Primary Examiner* — Matthew Lawson
*Assistant Examiner* — Zade Coley
(74) *Attorney, Agent, or Firm* — Tutunjian & Bitetto, P.C.

(57) ABSTRACT

A surgical device, in particular for percutaneous osteoplastic surgery, for example vertebroplastic operations or the like, and/or for biopsy operations, includes at least a guide for injection of a therapeutic fluid into a bony part, for example a cementing fluid, a needle being slidable internally of said guide, which needle having a first end provided with a gripping knob, and a second end opposite the first end, the guide having a first end which defines an obliquely-shaped dispensing opening of the fluid internally of the bony part, and a second end which defines a loading opening of the fluid at the outside of the bony part, the second end including a grip exhibiting two wings having different shapes, such that the position and orientation of the oblique profile of the opening can be recognized.

17 Claims, 5 Drawing Sheets

(56) References Cited

U.S. PATENT DOCUMENTS

| | | | | |
|---|---|---|---|---|
| 3,216,600 | A * | 11/1965 | Dreps | 215/230 |
| 3,980,194 | A * | 9/1976 | Costa | 215/223 |
| 4,796,615 | A * | 1/1989 | Bullock et al. | 128/202.27 |
| 5,171,223 | A * | 12/1992 | Herzberg | 604/104 |
| 6,162,197 | A * | 12/2000 | Mohammad | 604/195 |
| 6,221,029 | B1 * | 4/2001 | Mathis et al. | 600/564 |
| 6,302,868 | B1 * | 10/2001 | Mohammad | 604/192 |
| 6,383,190 | B1 * | 5/2002 | Preissman | 606/94 |
| 6,582,446 | B1 * | 6/2003 | Marchosky | 606/167 |
| 6,613,018 | B2 * | 9/2003 | Bagga et al. | 604/187 |
| 6,669,671 | B1 * | 12/2003 | Mohammad | 604/195 |
| 6,749,595 | B1 * | 6/2004 | Murphy | 604/500 |
| 6,875,219 | B2 * | 4/2005 | Arramon et al. | 606/92 |
| 7,544,196 | B2 * | 6/2009 | Bagga et al. | 606/93 |
| 2002/0120240 | A1 * | 8/2002 | Bagga et al. | 604/264 |
| 2007/0118142 | A1 * | 5/2007 | Krueger et al. | 606/92 |

FOREIGN PATENT DOCUMENTS

| | | | | |
|---|---|---|---|---|
| WO | WO 2007024641 | A2 * | 3/2007 | A61B 17/34 |
| WO | WO 2008010011 | A1 * | 1/2008 | |

* cited by examiner

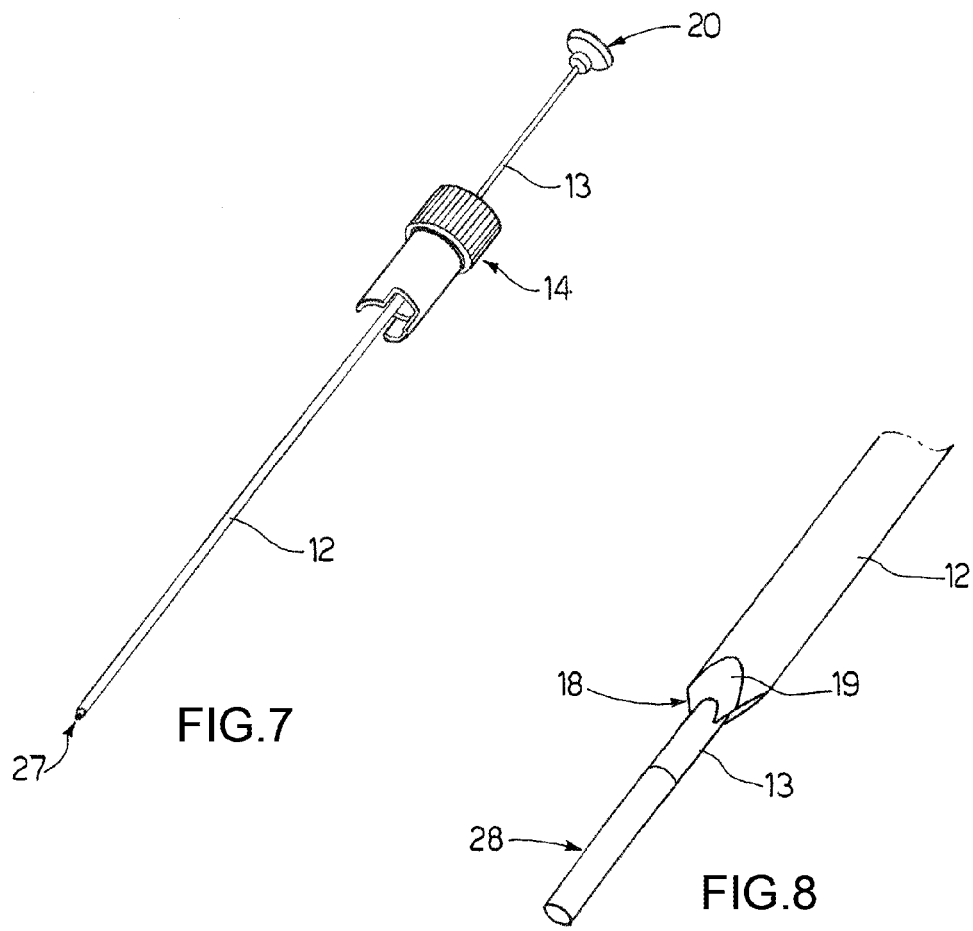
FIG.7
FIG.8
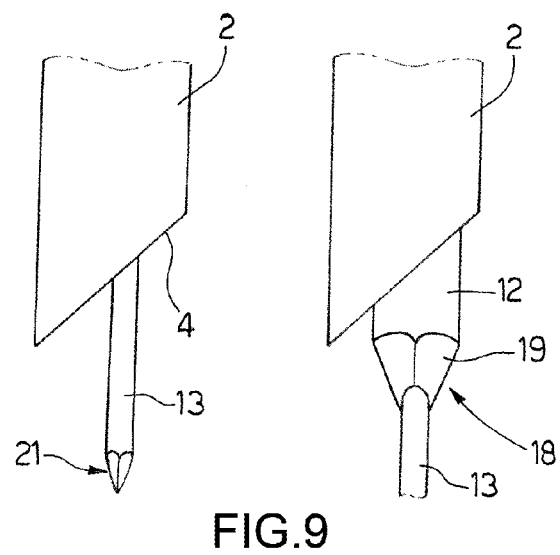
FIG.9

SURGICAL DEVICE

TECHNICAL FIELD

The invention relates to a surgical device, and in particular, in an aspect thereof, the present inventions relates to a biopsy needle for hard tissues, such as for example bone tissue, and in a further aspect thereof, the invention relates to a needle for percutaneous osteoplastic surgery/in particular for vertebroplastic operations.

DESCRIPTION OF RELATED ART

The prior art comprises various surgical devices, such as for example needles for hard-tissue biopsy, needles for introduction of fluid for vertebroplastic, needles for vertebrae fusion operations, etc.

U.S. Pat. No. 2,919,692 describes an instrument mainly usable for vertebral biopsy. The instrument of this patent comprises a tubular guide provided externally with a graduated scale for indicating the desired depth of penetration, a perforator, also tubular, insertable internally of the tubular guide, and a guide point for the perforator. The perforator has a jagged end for cutting the bone and a length such as to be able to reach the bone marrow. Further provided are other needles for preparing the perforating and needles of various lengths for obtaining biopsies at different depths.

In the use of this instrument, it is therefore necessary to introduce and extract the various guides and needles various times up to obtaining the biological material for the biopsy.

US patent US-2007/0270896 describes an access device to the peduncles of a vertebra to perform a vertebra fusion operation. The device comprises a tubular positioning needle, provided with a point which is particularly suitable for blocking on a peduncle of a vertebra; internally of the tubular needle there is a further needle provided with a point specially sharpened such as to penetrate through the peduncle. In an embodiment of the invention the point of the penetrating needle is pyramid-shaped, with three surfaces.

The penetrating needle is then extracted and a Kirschner wire is positioned; then the tubular positioning needle is removed and via successive stages of insertion and removal of the Kirschner wire and the positioning needle, threaded inserts are screwed into the vertebrae in order to fuse them.

SUMMARY OF THE INVENTION

An aim of the present invention is to improve the prior art.

A further aim of the present invention is to provide a surgical device which is easy and practical to use, for example in order to pass through the soft tissues of a patient.

A still further aim of the present invention is to provide a surgical device which enables biopsies to be performed and to realise osteoplastic surgery, in particular vertebroplastic operations, with a single instrument and in a single stage of insertion into the patient's body.

In an aspect of the invention, a surgical needle is used as in claim 1.

BRIEF DESCRIPTION OF THE DRAWINGS

Further characteristics and advantages of the invention will better emerge from the description of some embodiments of surgical devices, illustrated by way of example in the accompanying figures of the drawings, in which:

FIG. 7 is a perspective view of a surgical device of the present invention, during a stage of use in a biopsy;

FIG. 8 is a perspective view of a detail of the surgical device of FIG. 6;

FIG. 9 illustrates two lateral views of some details of the surgical device of the preceding figures;

DETAILED DESCRIPTION OF PREFERRED EMBODIMENTS

With reference to FIGS. 1-9, 1 denotes in its entirety a version of the surgical device of the present invention, in particular a device for osteoplastic surgery, such as vertebroplastic operations or the like, and for biopsy operations.

In the illustrated embodiment explicit reference to biopsy and osteoplastic surgery will be made, with introduction of bone cement applied to vertebrae, although it is understood that the present invention can also be applied to other types of bone operations.

The device 1 comprises a guide 2 provided with a first end 3 which is open and an edge of which defines a dispensing opening 4, the end 3 also being obliquely shaped.

Figure 6:
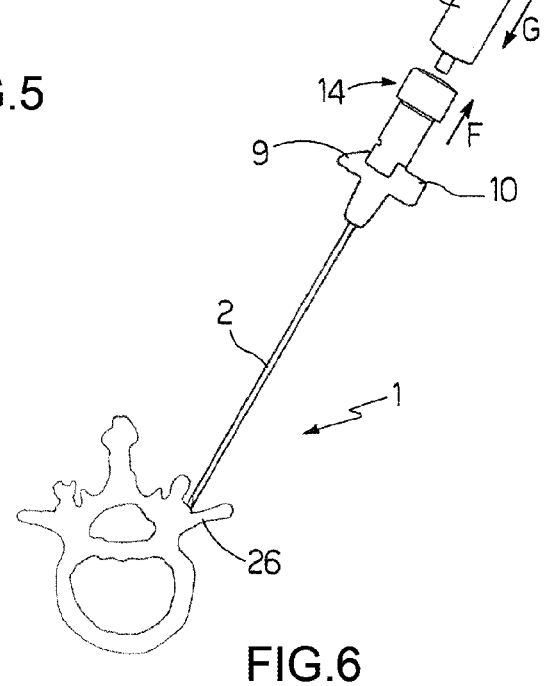

The guide 2 comprises, on an opposite side thereof with respect to the first end 3, a second end 5, also open; which defines the loading opening and which has connecting means 6 for a container tank 7 of therapeutic fluid, for example a cementing fluid (FIG. 6).

On the side of the second end 5, the guide 2 comprises a grip 8 which has two wings 9 and 10 having different shapes. According to what is illustrated in detail also in FIGS. 10-13; which relate to a further version of the guide 2 which will be described in greater detail herein below, the wing 9 has a triangular shape at the oblique dispensing opening 4, while the other wing 10 opposite the wing 9 has a rectangular shape. The shapes of the wings 9 and 10 described and illustrated herein are merely example embodiments and it is understood that other shapes destined to differentiate the two wings are possible, without forsaking the ambit of protection of the present invention.

Figures 10, 12:
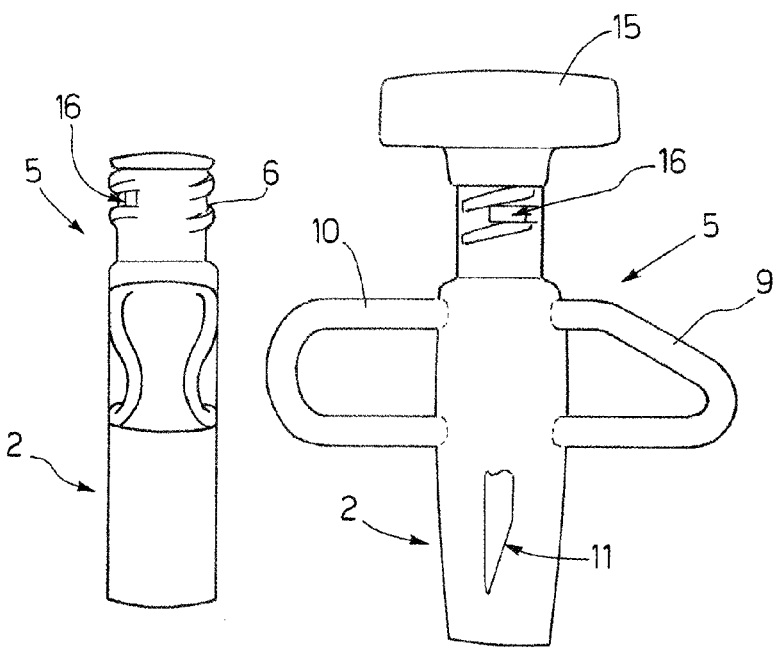
FIGS. 10 to 14 are enlarged views of some details of a further version of the device of the present invention.

As can be seen in FIG. 12, the guide 2 can comprise a symbol 11 which reproduces the position of the oblique shape of the opening 4. In the use of the guide 2, the operator can thus easily and safely orientate the position of the opening 4 such as to direct the cementing fluid in the desired direction.

According to what is illustrated in greater detail in FIGS. 3 and 7-9, a needle 12 can slide internally of the guide 2, which needle 12 is in turn axially hollow and internally comprises, in the axial cavity thereof, a spindle 13. The needle 12 comprises a first end 14 provided with a gripping knob 15, and first coupling means 16 destined to couple with second coupling means 17 of the guide 2.

The needle 12 further comprises a second end, or point 18, located on the opposite side to the first end 14, provided with a conical-shaped point 19 (not illustrated), or diamond-shaped with a pyramidal profile having two or more surfaces.

The spindle 13 too comprises a first end provided with a knob 20 and a second end, opposite the first end, with a conical-shaped point 21 (not illustrated), or diamond-shaped with a pyramidal profile having two or more surfaces.

The first and the second coupling means 16, 17 enable two different relative positions to be achieved between the guide 2 and the needle 12. In a first relative position, illustrated in FIG. 3, the point 18 of the needle 12 projects with respect to the oblique profile of the opening 4.

This first relative position enables a greater penetration of the guide 2 and needle 12 group into the soft tissues of the patient, thanks to the prominence of the conical or diamond-shaped point 18.

A second relative position between the guide 2 and the needle 12 envisages the oblique end 3 being projecting with respect to the point 18 of the needle 12.

This second relative position enables a greater penetration of the guide 2 and needle 12 group into the hard tissues of the patient, in particular into the bone tissues such as, for example, the vertebrae.

In order to attain the two positions, the first coupling means comprise a groove 16 comprising two portions 22, 23 arranged, on a cylindrical part of the end 14 of the needle 12, at two different axial depths. The second coupling means of the guide 2 comprise a pin 17 destined to insert in the groove 16. The groove 16 and the pin 17 constitute together a bayonet coupling with two different positions of the needle 12 with respect to the guide 2. When the needle 12 is in the position with the point 18 projecting further than the guide 2, the pin 17 is inserted in portion 22, while in the other position, with the point 18 retracted with respect to the guide 2, the pin 17 is inserted in portion 23.

The groove 16 further comprises an open axial section 24 through which the pin 17 is inserted.

In the version illustrated in FIGS. 10 to 14, the positions of the pin 17 and the groove 16 are exchanged.

Figure 14:
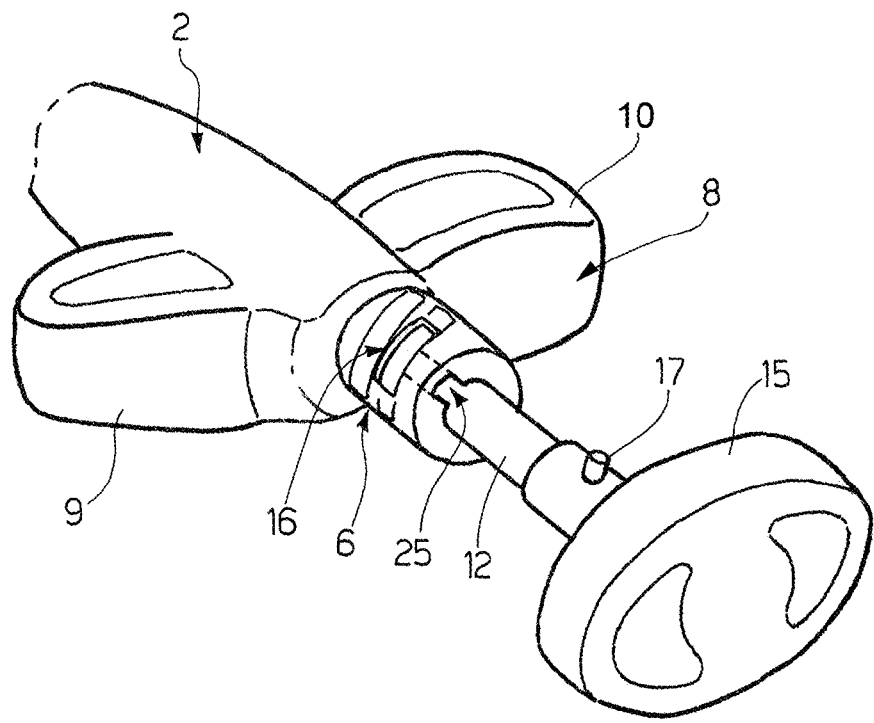

The pin 17 is in proximity of the gripping knob 15 on the needle 12, while the guide 2 comprises a partially-closed groove 16, and in particular in FIG. 14, the groove 16 comprises an axial section 25 which is closed on top through which the pin 17 is inserted. The end 6 of the guide 2 is ring-closed and is therefore very resistant.

The groove 16 illustrated in FIGS. 10-14 has a single axial position of the needle 12 because it relates to a simplified version of the present invention.

Figure 1:
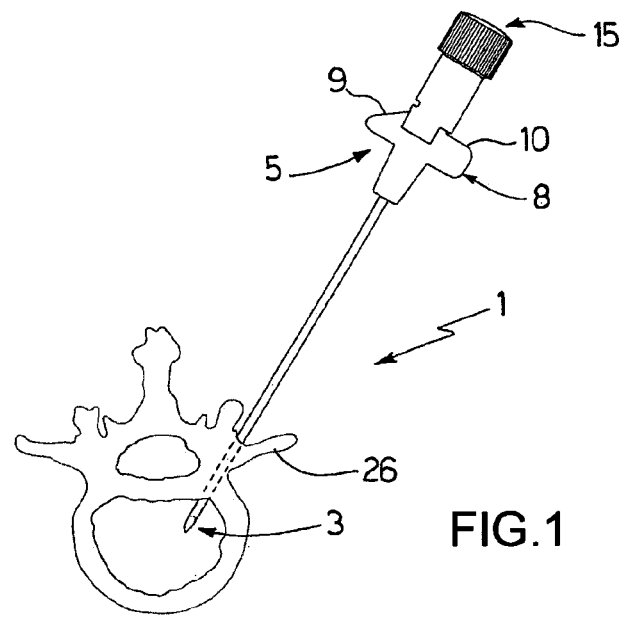
FIG. 1 is a perspective view of a surgical device of the present invention, during a stage of use in a vertebroplastic operation.
Figure 2:
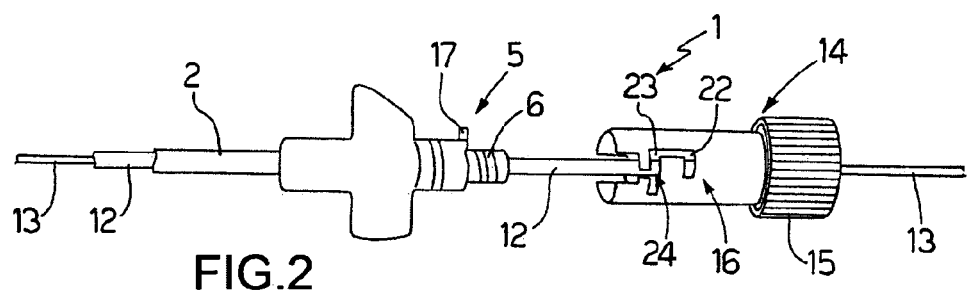
FIG. 2 is a lateral view of a detail of the surgical device of FIG. 1.
Figure 3:
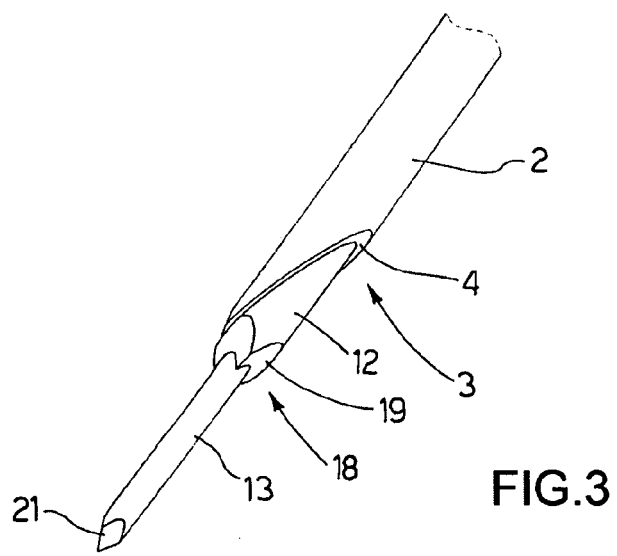
FIG. 3 is a perspective view of a further detail of the surgical device of FIG. 1.
Figure 4:
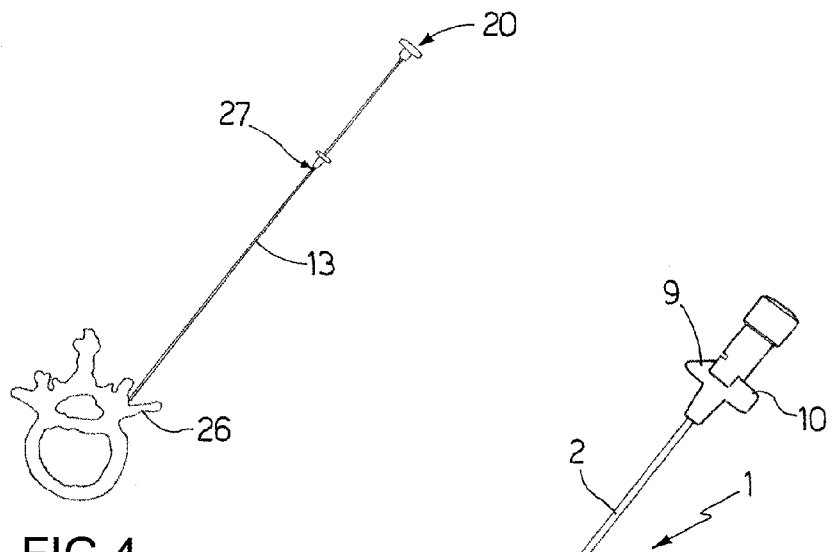
FIGS. 4 to 6 illustrate some stages of use, in a vertebroplastic operation, of the surgical device of the present invention.
Figure 5:
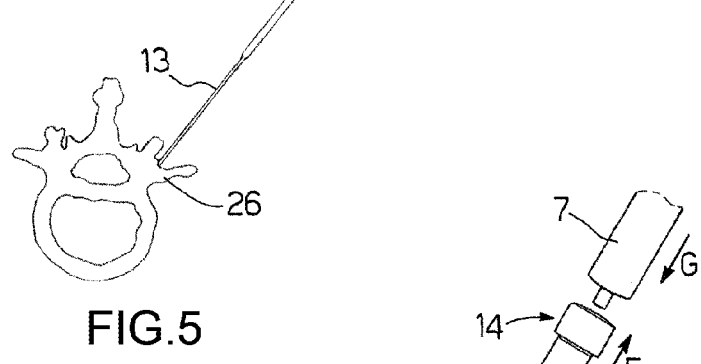

However, the groove 16 illustrated in FIG. 2, with two sections 22, 23 arranged at different axial depths, can be applied to the end 6 of the guide 2 illustrated in FIGS. 10-14.

Figures 11, 13:
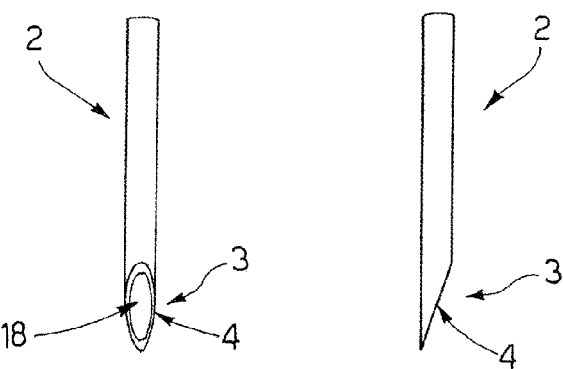

In the simplified version, the end 18 of the needle 12 also exhibits an oblique shape. When the pin 17 of the needle 12 is completely inserted in the groove 16 of the guide 2, the end 18 integrates, practically without interruption, with the opening 4 (FIG. 11).

In the more complete version of the device 1, illustrated in FIGS. 1-9, during a surgical operation, the operator first inserts the spindle 13 into the body of the patient up to reaching and stopping against a bony part 26 (FIG. 4) which is the objective of the surgical operation.

To facilitate introduction of the spindle 13 in the patient's body, the operator can use a spindle guide 27. The introduction of the spindle is also facilitated by the small diameter of the spindle 13 itself and by the conical or diamond shape of the point 21. This type of conical or diamond-shaped point is particularly suitable for cutting the soft tissues of the patient without there being deviations from the setting provided by the operator.

The guide 2 and needle 12 group is then introduced by sliding it on the spindle 13, with the point 19 of the needle 12 in the most projecting position (FIGS. 3 and; 5) up to halting it against the bony part 26 (FIG. 6). In this case too, the conical or diamond-shaped configuration 19 of the point 18 facilitates penetration into the patient's soft tissues without any deviation from the setting desired by the operator.

Then in order to proceed to penetration into the bony part 26 the operator positions the needle 12 and the relative point 18 in the retracted position, moving the pin 17 to the portion 23 of the groove 16.

In this way, it is the oblique end 3 which penetrates into the bony part 26 as the oblique shape is more favorable for penetration into the hard tissues, such as, in this case, the bony parts.

Note that thanks to the triangular-shaped wing 9 of the grip 8, the operator can easily and safely orientate the position of the opening 4 which is positioned at said wing 9.

During the penetration into the bony part 26, and in order to carry out a biopsy of said bony part 26; the spindle 13 is placed in a retracted position with respect to the needle 12.

The end 18 of the needle 12 facing towards the bony part 26 exhibits a cavity 27 corresponding to the portion left free by the spindle 13. During the introduction into the bony part 26; thanks to the cutting edge of the end 18, the cavity 27 fills with bony material 28.

When the guide 2 has completely penetrated into the bony part 26 (FIG. 1), with the end 3 in the correct position for effecting an introduction of therapeutic fluid, for example cementing fluid for osteoplastic surgery, the operator can extract (FIG. 6, arrow F) the needle 12 with the spindle 13 (FIG. 7).

The container tank 7 of cementing fluid can therefore be applied (FIG. 6, arrow G) via the connecting means 6 and the osteoplastic operation, in particular a vertebroplastic operation, can commence.

According to what is illustrated in FIG. 8, by reinserting the spindle 13 into the needle 12, the bony material 28 of the biopsy can be extracted.

From the sequence of operations as described above, it is evident that it is possible to obtain the biopsy of the bony part 26 without further introductions and/or extractions of the device 1; while at the same time an osteoplastic operation; especially a vertebroplastic operation, can be carried out.

With the simplified version of the device 1, illustrated in FIGS. 10-14, therapeutic fluids can be introduced into the bony part, for example vertebroplastic surgery with introduction of cementing fluid, but a biopsy of the bony tissue cannot be carried out.

The guide 2 with the needle 12 are initially fixed together such as to have the end 18 of the needle 12 integrated, practically without interruption, with the opening 4 of the guide 2 (FIG. 11). This position is obtained by means of the bayonet coupling between the guide 2 and the needle 12 at the opposite end of the oblique opening. As already indicated the bayonet coupling of this version of the device 1 comprises a ring-closed end, though comprising a slot 16 with an axial section 25 closed at the top, through which the pin 17 borne by the needle 12 is inserted. The end 6 of the guide 2 is ring-closed and is therefore very resistant.

Once the device 1 is introduced into the patient's bony part; the operator can extract the needle 12; rotating and releasing from the bayonet coupling; and can thus apply the container tank 7 of cementing fluid; via the connecting means 6, and proceed with the osteoplastic percutaneous operation, in particular a vertebroplastic operation.

The invention claimed is:

1. A surgical device for at least one of percutaneous osteoplastic surgery including vertebroplastic operations and for biopsy operations with a single device and in a single stage of insertion into the patient's body, comprising at least a guide for the injection of a therapeutic fluid into a bony part, a needle being slidable internally of said guide, said needle having an axial hollow, a first end provided with a gripping knob, and a second end, opposite said first end, said guide having a first end which defines at least a dispensing opening of said fluid internally of said bony part, and at least a second end which defines a loading opening of said fluid at the outside of said bony part, said dispensing opening being obliquely shaped, wherein said second end comprises a grip, which grip exhibits two wings having different shapes, such that the position and orientation of the oblique profile of the opening can be recognized and the operator can thus easily and safely orientate the position of the opening such as to direct the cementing fluid in the desired direction; and
 a spindle slidably inserted in the axial hollow of said needle, wherein the guide, the needle and the spindle are co-axial and wherein the first end of the needle includes bayonet coupling means for affixing the guide with the needle and providing two different relative positions of the needle relative to the guide when the needle and the guide are affixed, wherein said bayonet coupling means comprises a continuous groove formed on said first end of the needle, said continuous groove comprising two opposing portions arranged along opposite ends of the continuous groove, the two opposing portions defining two different axial depths to enable fastening said needle at two different set axial positions of the needle with respect to said guide.

2. The device of claim 1, wherein said guide and said needle are fixable together such that the second end of the needle is integrated, substantially without interruption, with the dispensing opening of the guide.

3. The device of claim 1, further comprising bayonet coupling means positioned on said second end of said guide and said first end of said needle.

4. The device of claim 3, wherein said bayonet coupling means comprises a pin arranged on one of said second end of said guide and said first end of said needle.

5. The device of claim 3, wherein said bayonet coupling means comprise a groove arranged on one of said second end of said guide and said first end of said needle, and wherein one of said second end of said guide and said first end of said needle is shaped like a closed ring.

6. The device of claim 5, wherein said groove comprises an axial section which is closed at the top.

7. The device of claim 1, wherein said second end of said needle has a point which is conical or diamond-shaped having a pyramidal profile exhibiting two or more surfaces.

8. The device of claim 7, wherein said point of said needle is positionable in a more projecting position with respect to said obliquely-shaped dispensing opening.

9. The device of claim 8, wherein said point of said needle is positionable in two positions, at different axial depths with respect to said guide, through said bayonet coupling means.

10. The device of claim 1, wherein said spindle comprises a point which is conical or diamond-shaped having a pyramidal profile exhibiting two or more surfaces.

11. The device of claim 1, wherein said spindle comprises a knob destined to enable the introduction of the spindle into the patient's body.

12. The device of claim 1, wherein said second end of the guide, which defines a loading opening of said therapeutic fluid, comprises connecting means for a container tank of said fluid.

13. The device of claim 1, wherein the therapeutic fluid comprises a cementing fluid.

14. A surgical device comprising:
 a guide having an axial hollow, a first end which defines an oblique end having a dispensing opening, and a second end which defines a loading opening;
 a needle slidably inserted in said axial hollow of said guide, said needle having an axial hollow, a first end, and a second end including a point; and
 a spindle slidably inserted in the axial hollow of said needle, wherein the guide, the needle and the spindle are co-axial and wherein the first end of the needle includes a continuous groove formed thereon for affixing the guide with the needle and comprising two opposing portions arranged along opposite ends of the continuous groove, the two opposing portions defining two different set positions of the guide relative to the needle when the needle and the guide are affixed.

15. The device of claim 14, wherein the first set position comprises wherein the point of the needle projects with respect to the oblique end.

16. The device of claim 14, wherein the second set position comprises wherein the oblique end projects with respect to the point of the needle.

17. The device of claim 14, further comprising a container tank, wherein the needle and the spindle are removed from the guide and the container tank is applied to the guide.

\* \* \* \* \*